United States Patent

Atwood et al.

Patent Number: 5,489,612
Date of Patent: Feb. 6, 1996

[54] CALIXARENE CHLORIDE-CHANNEL BLOCKERS

[75] Inventors: Jerry L. Atwood, Tuscaloosa; Robert J. Bridges, Birmingham; Ravindra K. Juneja, Tuscaloosa; Ashvani K. Singh, Birmingham, all of Ala.

[73] Assignee: The University of Alabama at Birmingham Research Foundation, Birmingham, Ala.

[21] Appl. No.: 178,610

[22] Filed: Jan. 7, 1994

Related U.S. Application Data

[63] Continuation of Ser. No. 748,764, Aug. 23, 1991, abandoned.
[51] Int. Cl.$^6$ ............ A61K 31/19; A61K 31/185; A61K 31/165; A61K 31/10
[52] U.S. Cl. ............ 514/569; 514/577; 514/618; 514/709
[58] Field of Search ............ 424/78.08; 514/569, 514/577, 618, 709; 562/88, 492

[56] References Cited

U.S. PATENT DOCUMENTS

| | | | |
|---|---|---|---|
| 4,617,336 | 10/1986 | Pastor et al. | 524/291 |
| 5,206,437 | 4/1993 | Morita | 564/310 |
| 5,312,837 | 5/1994 | Hwang et al. | 514/577 |

OTHER PUBLICATIONS

Mahendra Kumar et al., Biochem. J. (1985) 227 789–794.

*Primary Examiner*—Raymond Henley, III
*Attorney, Agent, or Firm*—Benjamin Aaron Adler

[57] ABSTRACT

Calixarene derivatives, their synthesis and use as chloride channel blockers are described. Preferred calixarene derivatives are of the formula:

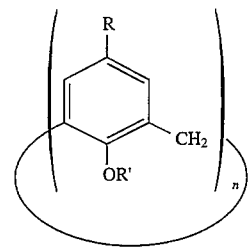

wherein R is an acidic group or salt thereof, such as $SO_3X$ or $R^1SO_3X$ where X is H or Na, and $R^1$ is

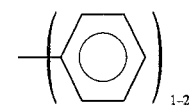

where m=1–2, and $R^3$ and $R^4$ the same or different is each H or a $C_{1-4}$ alkyl, or a nitrogen-containing group of the formula

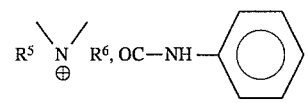

or A,
wherein $R^5$ is a $C_{1-4}$ alkyl, $R^6$ is a $C_{1-4}$ alkyl and A is

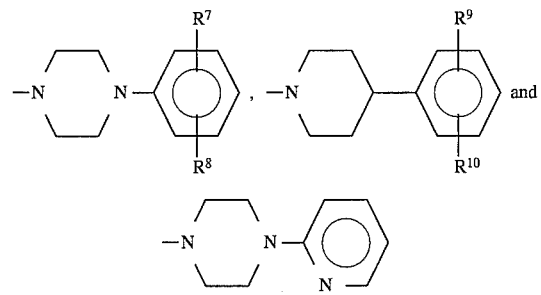

where $R^7$ and $R^8$, the same or different each is H or a $C_{1-4}$ alkyl, and $R^9$ and $R^{10}$, the same or different, each is H or a $C_{1-4}$ alkyl; R' is H or a $C_{1-4}$ alkyl; and n is an integer of 4–8, preferably 4, 6 or 8.

8 Claims, No Drawings

CALIXARENE CHLORIDE-CHANNEL BLOCKERS

This application is a continuation of U.S. application Ser. No. 07/748,764 filed Aug. 23, 1991, now abandoned.

BACKGROUND OF THE INVENTION

Calixarenes are complex compounds containing a $[1_n]$ metacyclophane framework. Although some applications for some types of calixarene compounds have been developed, research into calixarene chemistry is still progressing. See Gutsche, *Calixarenes*, Royal Soc. Chem., 1989. The present inventors have synthesized new calixarene derivatives, and have developed an important application for some calixarene derivatives as chloride channel blockers.

All cell types have chloride channels. Chloride ion channels are transport proteins that allow for the rapid (i.e., $10^{6-108}$ ions/second) entry and exit of chloride across the plasma membrane. Based on their distribution in various cell types and their biophysical as well as functional diversity, chloride channels may serve as molecular targets for effective pharmaceuticals in a variety of applications.

Chloride channels subserve a wide variety of specific cellular functions. It is known that abnormal chloride permeability in skeletal muscles plays a part in some forms of myotonia. Thus, chloride channels contribute to the normal function of skeletal and smooth muscle cells. Additionally, the contribution of chloride channels in fluid and electrolyte secretion is well documented in the physiology of epithelia. Further, patients suffering from cystic fibrosis exhibit effects caused by too few open chloride channels, while patients suffering from diarrhea demonstrate the acute effects of too many open chloride channels.

Thus, in general, chloride channel modulators may serve as effective pharmaceuticals for treating respiratory, cardiovascular and gastrointestinal disorders. Specific therapeutic applications for chloride channel modulators include the treatment of asthma, hypertension, cancer, diabetes, ischemia, muscle fatigue, edema, diarrhea, cystic fibrosis and myotonia.

Only a few substances have been found that affect chloride channels. Chloride channel blockers that have been developed include 5-nitro-2-(3-phenylpropylamino)benzoic acid (NPPB), 2-[(2-cyclopentyl-6,7-dichloro-2,3-dihydro-2-methyl-1-oxo-1H-inden-5-yl)oxy] acetic acid (IAA-94) and 4,4'-dinitrostilbene-2,2'-disulfonic acid (DNDS). See, Singh et al., "Colonic Cl Channel Blockade by Three Classes of Compounds", *Am. J. Physiol.* 261 (*Cell Physiol.* 30): C51–C63, 1991.

Although various carboxylic and sulfonic organic acids have been tested as chloride modulators, heretofore there has not been developed a highly potent and specific chloride channel modulator causing long-lived block periods at low concentrations.

SUMMARY OF THE INVENTION

An object of this invention is to provide novel calixarene derivatives and a method of making them. Another object is to provide a treatment for effective modulation or blockage of chloride channels. Another object of the invention is to provide a class of highly potent chloride channel blockers which cause block periods of long duration. A further object of the present invention is to provide an effective chloride channel blocker which is effective at low concentrations.

The present invention relates to calixarene compounds useful as effective chloride channel modulators. More specifically, this invention relates to the synthesis of highly-potent calixarene channel-blocker compounds, compositions thereof and the use of such compounds and compositions.

DESCRIPTION OF PREFERRED EMBODIMENTS

The present inventors have found that calixarenes having an acidic group, e.g., p-sulfonato-calix[n]arenes and other calixarenes with p-acid functionality, serve as potent blockers of colonic chloride channels. These calixarene compounds have the following structure:

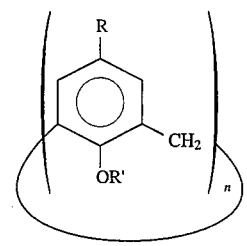

wherein:

R is an acidic group such as $SO_3X$, $R^1SO_3X$, sulfonamide, $COOX$ or $R^1COOX$ wherein X is H, Na, K, Rb, Cs, Li, $NH_4^+$, $N(R_i)_4^+$, with $R_i$ being H, a $C_{1-4}$ alkyl, aryl such as phenyl and naphthyl, or a combination thereof, and $R^1$ is

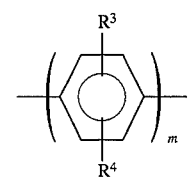

where m=1–2, and $R^3$ and $R^4$, the same or different, are selected from H or a $C_{1-4}$ alkyl, a $C_{1-4}$ alkoxy or $R^1$ is a nitrogen-containing group selected from

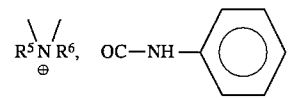

and A,
wherein $R^5$ is a $C_{1-4}$ alkyl, $R^6$ is a $C_{1-4}$ alkyl or a $C_{1-4}$ alkoxy, and A is selected from

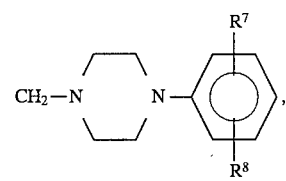

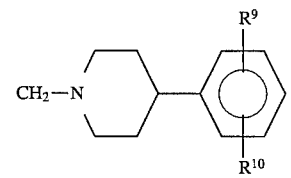

and

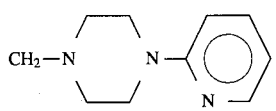

where $R^7$ and $R^8$, the same or different are H or a $C_{1-4}$ alkyl and $R^9$ and $R^{10}$, the same or different are H or a $C_{1-4}$ alkyl;

R' is a hydrogen atom, $C_{1-4}$ alkyl group, $C_{1-4}$ alkoxy group, acid group such as —$CH_2COOH$, ester group such as —$CH_2OOC_2H_5$, aryl group such as phenyl or naphthyl, or —$CH_2CONR^5R^6$ where $R^5$ and $R^6$ are as previously defined; and n is an integer of 4–8.

Preferably, R is $SO_3Na$ or $R^1SO_3Na$, $R^1$ is

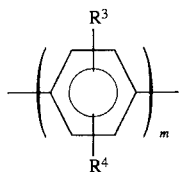

where m—1–2, and $R^3$ and $R^4$, the same or different are selected from H or a $C_{1-4}$ alkoxy or $R^1$ is a nitrogen-containing group selected from

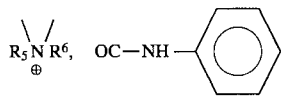

wherein $R^5$ is a $C_{1-4}$ alkyl, $R^6$ is a $C_{1-4}$ alkyl or a $C_{1-4}$ alkoxy, and A is selected from

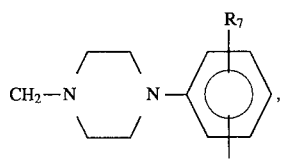

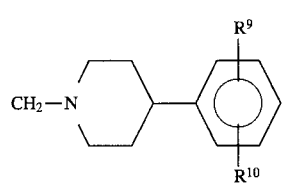

and

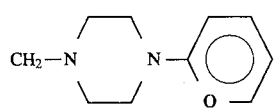

where $R^7$ and $R^8$, the same or different, are H or a $C_{1-4}$ alkyl, and $R^9$ and $R^{10}$, the same or different, are H or a $C_{1-4}$ alkyl; R' is H or a $CH_3$ group, and n is 4, 6 or 8. The OR' group can also be a mixture of, e.g., OH and OMe.

Preferred calixarene derivatives effective as chloride channel blockers are 5,11,17,23-tetrasulfonato-calix[4]arene and 5,11,17,23-tetrasulfonato-25,26,27,28-tetramethoxy-calix[4]arene (TS-TM-calix[4]arene). Other preferred derivatives useful as chloride channel blockers are 5,11,17, 23,29,35-hexasulfonatocalix[6]arene and 5,11,17,23,29,35, 41,47-octasulfonatocalix[8]arene.

Calixarene derivatives effective as chloride channel blockers may be prepared in accordance with the following general reaction scheme:

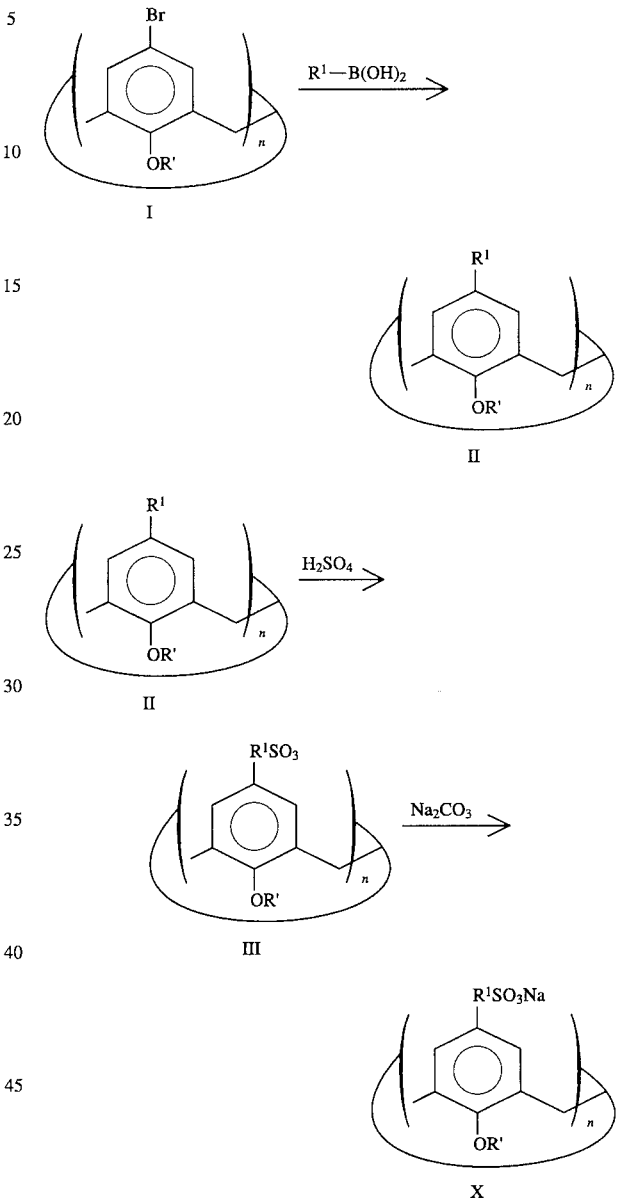

To a stirred solution of 1.5 mmol of the bromo-methoxy calixarene I and 0.2 mmol of $Pd(PPh_3)_4$ in 10 ml of toluene under nitrogen atmosphere, 5 ml of a 2M aqueous solution of $Na_2CO_3$ and 7.2 mmol of aryl boronic acid in 5 ml methanol are added. The vigorously stirred mixture is warmed to 80° C. for 6 hours, then cooled and partitioned between 50 ml of $CH_2Cl_2$ and 25 ml of 2M $Na_2CO_3$ containing 2.5 ml of $NH_3$. The organic layer is dried using $Na_2SO_4$ and concentrated under reduced pressure. Then the crude material thus obtained is subjected to column chromatography over silica gel, yielding calix[n]arene II.

The p-aryl methoxy calix[n]arene II is then slurried in water. The slurry is added to a concentrated $H_2SO_4$ solution and heated to 60° C. for 3 hours to produce compound III. Neutralization with $Na_2CO_3$ yields the calix[n]arene sulfonate X.

Another approach for synthesizing p-phenyl calixarenes is in accordance with the following general reaction scheme:

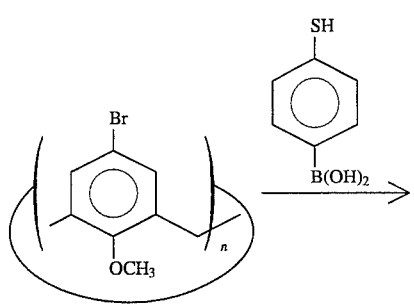

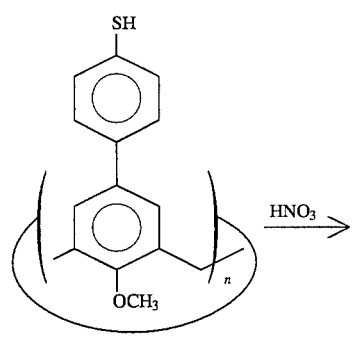

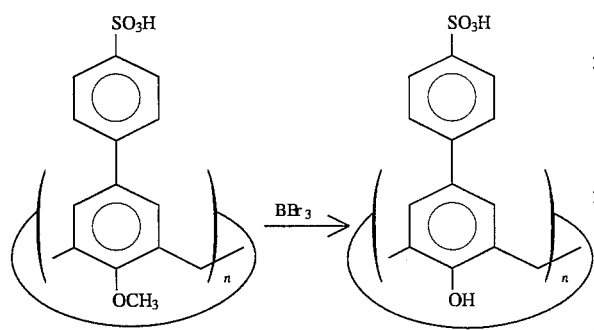

Syntheses of specific calixarene sulfonates in accordance with the invention are described by reference to the following examples.

EXAMPLES

Example 1a—Synthesis of the P-Aryl Methoxy Calixarene

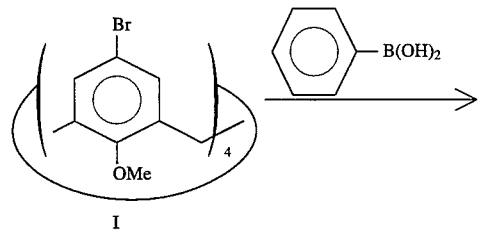

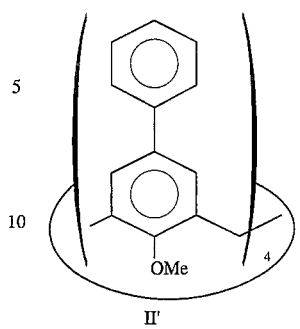

II'

Five ml of a 2M aqueous solution of $Na_2CO_3$ and 7.2 mmol of aryl boronic acid in 5 ml methanol were added to a stirred solution of 1.5 mmol of the bromo-methoxy calixarene I (1.194 g) and 0.2 mmol of $Pd(PPh_3)_4$ (0.231 g) in 10 ml of toluene under nitrogen atmosphere. The vigorously stirred mixture was warmed to 80° C. for 6 hours, then cooled and partitioned between 50 ml of $CH_2Cl_2$ and 25 ml of 2M $Na_2CO_3$ containing 2.5 ml of $NH_3$. The organic layer was dried using $Na_2SO_4$ and concentrated under reduced pressure. The crude material thus obtained was subjected to column chromatography over silica gel, yielding 1.094 g of pure product (75% yield) p-aryl methoxy calix[4]arene II'.

Example 1b—Synthesis of the P-Phenyl Calixarene Sulfonate

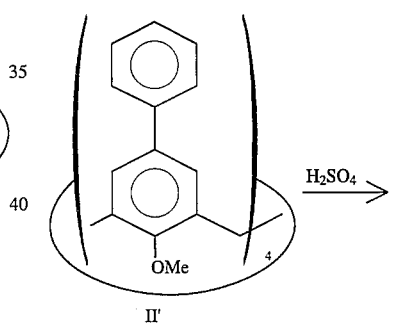

II'

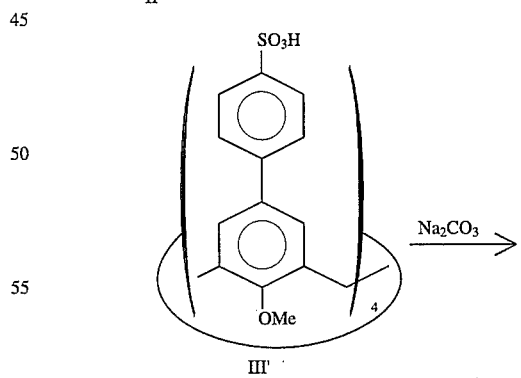

III'

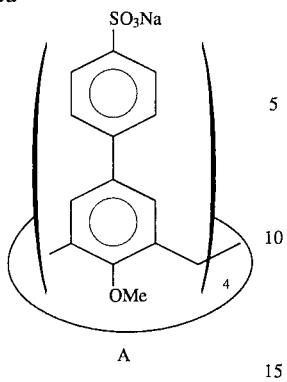

A 0.3 g of the p-aryl methoxy calix[4]arene II' obtained in Example 1a was stirred in 3 ml sulfuric acid and heated to 50° C. for 2.5 hours. The end of the reaction was when the reaction mixture became completely soluble in water. The reaction mixture of compound III' was cooled and added to 10 ml water. The mixture was neutralized with $Na_2CO_3$, yielding the calixarene sulfonate A.

Example 2a—Synthesis of the P-Aryl Methoxy Calixarene

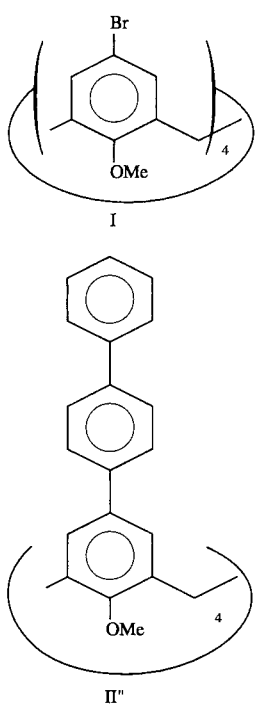

Five ml of a 2M aqueous solution of $Na_2CO_3$ and 7.2 mmol of aryl boronic acid in 5 ml methanol were added to a stirred solution of 1.5 mmol of the bromo-methoxy calixarene I (1.194 g) and 0.2 mmol of $Pd(PPh_3)_4$ (0.231 g) in 10 ml of toluene under nitrogen atmosphere. The vigorously stirred mixture was warmed to 80° C. for 6 hours, then cooled and partitioned between 50 ml of $CH_2Cl_2$ and 25 ml of 2M $Na_2CO_3$ containing 2.5 ml of $NH_3$. The organic layer was dried with $Na_2SO_4$ and concentrated under reduced pressure. The crude material thus obtained was subjected to column chromatography over silica gel, yielding 500 mg of the p-aryl methoxy calix[4]arene II'' (44% yield).

Example 2b—Synthesis of the P-Phenyl Calixarene Sulfonate

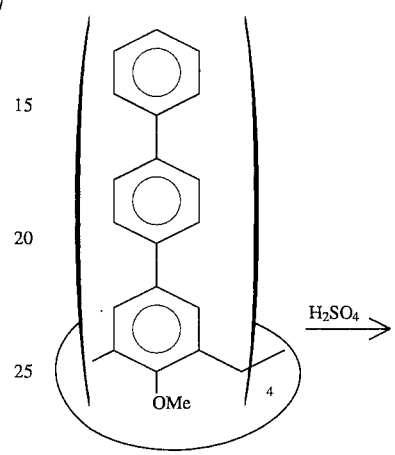

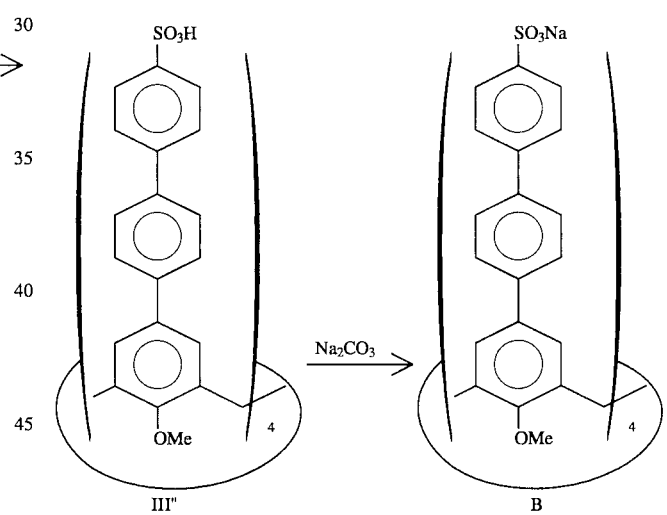

The p-aryl methoxy calix[4]arene II'' obtained in Example 2a was stirred in 3 ml sulfuric acid and heated to 50° C. for 2.5 hours. The end of the reaction was when the reaction mixture became water-soluble. The reaction mixture of compound III'' was cooled and added to 10 ml water. The mixture was neutralized with $Na_2CO_3$, yielding the calixarene sulfonate B.

Example 3

A calix[n]arene sulfonate C is prepared in accordance with the following reaction scheme:

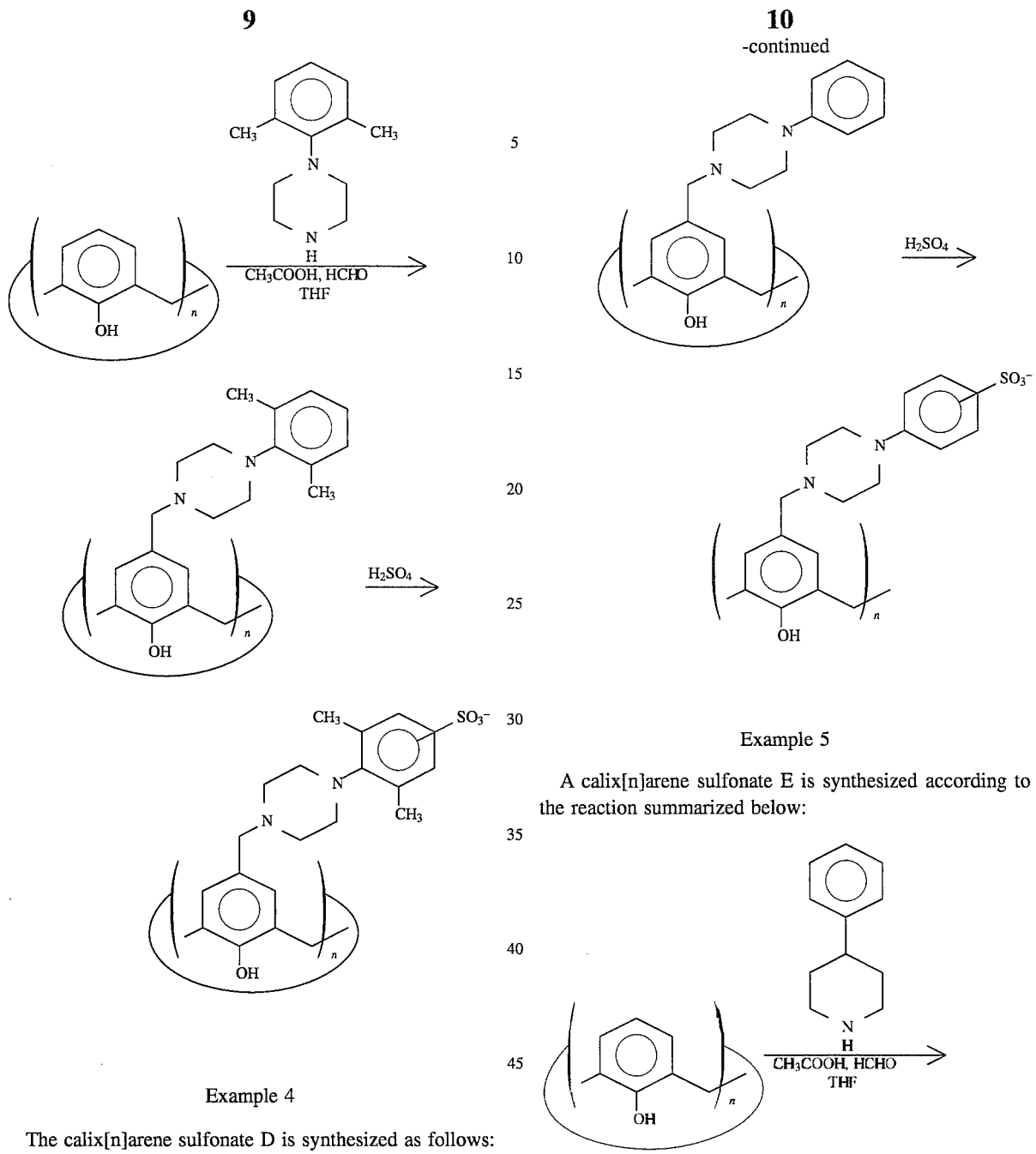
Example 4
The calix[n]arene sulfonate D is synthesized as follows:
Example 5
A calix[n]arene sulfonate E is synthesized according to the reaction summarized below:
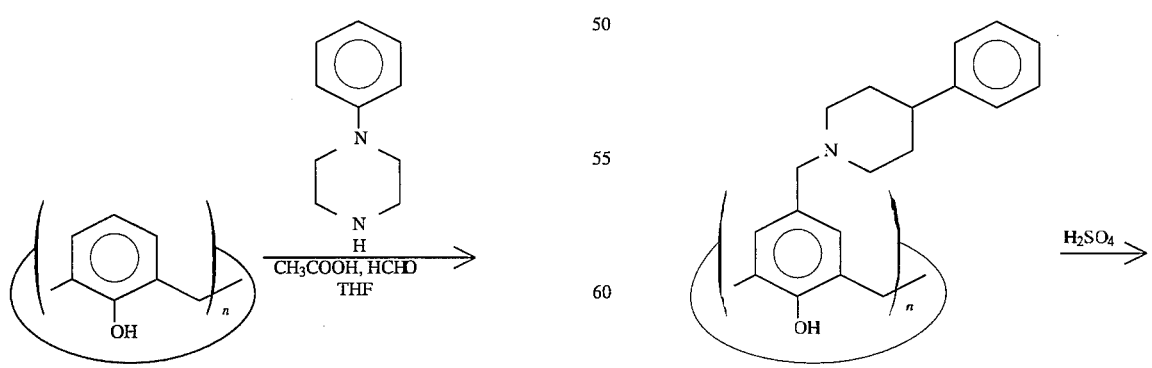

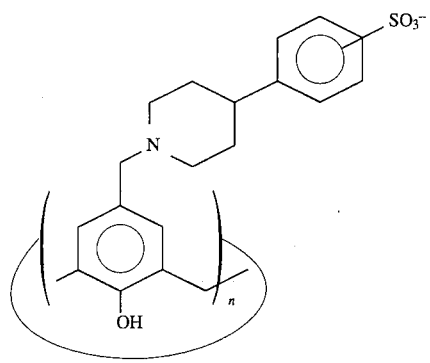
Example 6
The calix[n]arene sulfonate F is produced by following the general reaction scheme below:
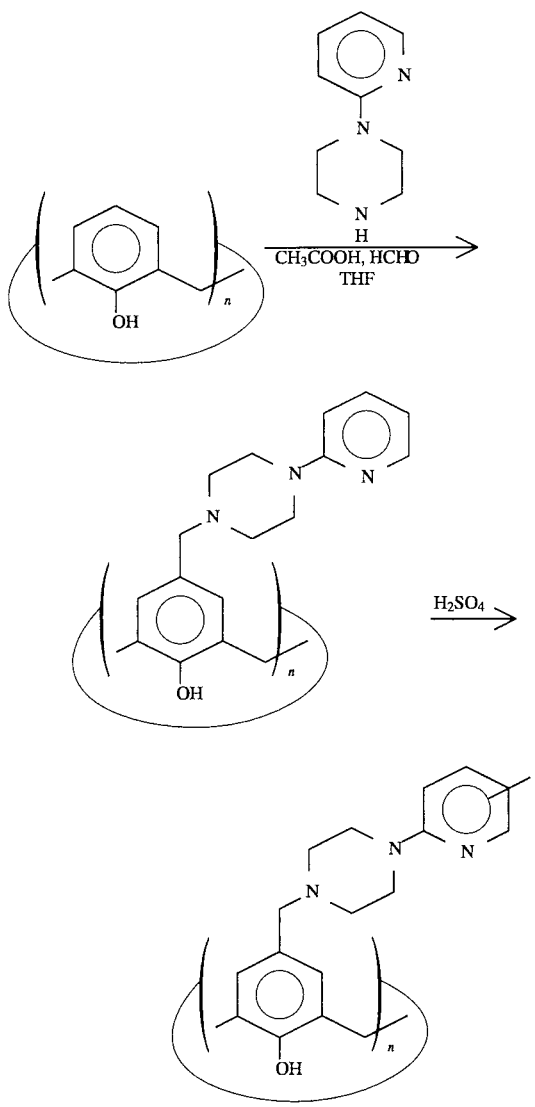
Example 7
A calix[n]arene sulfonate G is prepared as follows:
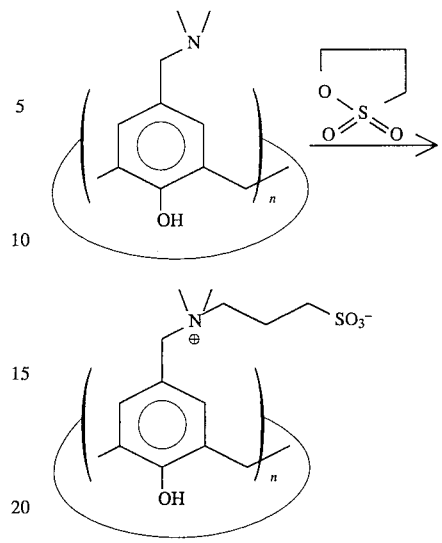
Example 8
The calix[n]arene sulfonate H is synthesized according to the following reaction:
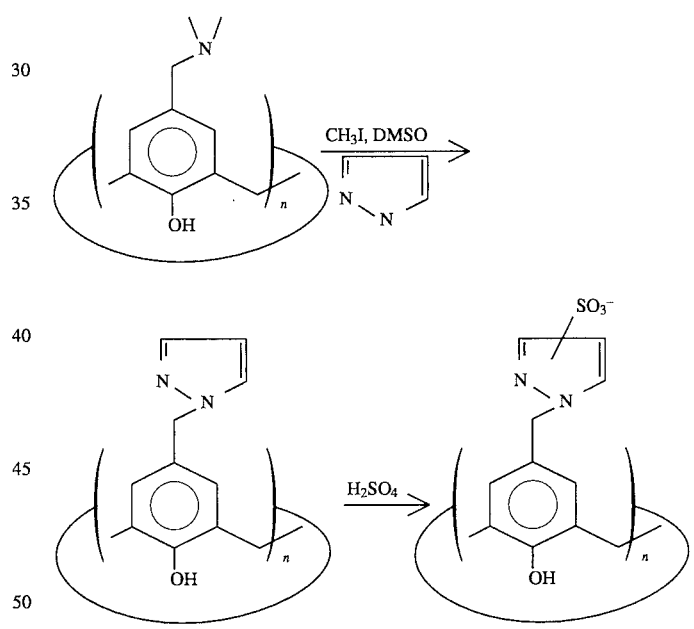
Example 9
A calix[n]arene sulfonate I is prepared by following the synthesis route summarized below:
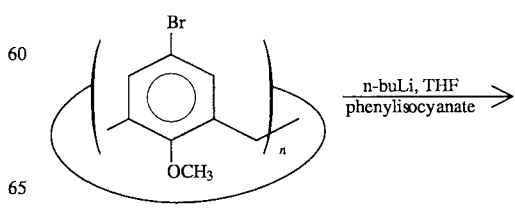

13
-continued

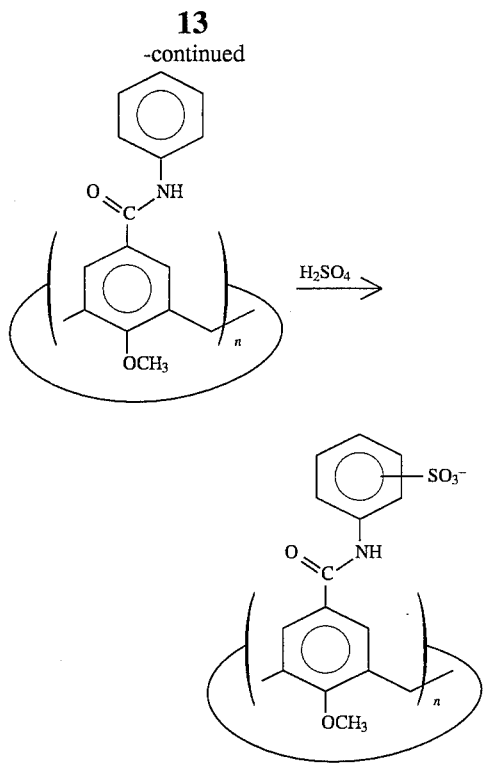

Testing for Chloride Channel Blockade

In accordance with the methodology of Reinhardt et al., "Properties of an Anion-selective Channel from Rat Colonic Enterocyte Plasma Membranes Reconstituted into Planar Phospholipid Bilayers", *J. Membrane Biol.* 95: 47–54, 1987, calixarene derivatives were tested on single chloride channels incorporated into planar lipid bilayers. Plasma membrane vesicles derived from rat colonic enterocytes were used as a source of chloride channels. Properties of the colonic secretory chloride channel include one dominant open-state conductance, an outwardly rectified current-voltage relation with a zero voltage slope conductance of 50 pS in 150 mM Cl, a Cl to Na selectivity of at least 10:1, and a halide selectivity of I>Br>Cl>F. Patch-clamp studies of several chloride secreting epithelia have identified an apical membrane chloride channel with identical biophysical properties. This channel is activated by cAMP and Ca mediated agonists and thus is considered a secretory chloride channel.

Chloride channels were incorporated into planar lipid bilayers of phosphatidylethanolamine and phosphatidylserine (PE:PS, 7:3) and data recorded according to known test methodology. See, Bridges et al., "Stilbene Disulfonate Blockade of Colonic Secretory Cl⁻ Channels in Planar Lipid Bilayers", *Am. J. Physiol.* 256 (*Cell Physiol.* 25): C902–C912, 1989. See also, Reinhardt et al. and Singh et al., supra.

14

Once a chloride channel was incorporated into the bilayer, baseline (control) channel activity was recorded for 5–15 minutes. The calixarenes were then added to the cis or outer membrane side of the channel and the channel activity recorded for an additional 5–15 minutes at each concentration. Because each channel serves as its own control, calixarene effects could be uniquely identified. In some experiments the cis compartment was exchanged with calixarene-free solution to test the reversibility of the calixarene-induced effects. Single channel records were stored on with calixarene-free solution to test the reversibility of the calixarene-induced effects. Single channel records were stored on video tape and quantitatively evaluated by computer assisted analysis.

The p-sulfonato-calixarenes resulted in long-lived zero conductance closures (i.e., block) of the colonic chloride channel. Chloride channel blockade by the calixarenes was completely reversed upon exchange of the cis compartment with calixarene-free buffer. The duration of the block periods caused by the calixarenes increased with the size of the p-sulfonatocalix[n]arene as follows: n=4, 3–4 seconds; n=6, 30–40 sec.; n=8, >>100 sec. The block periods induced by the p-sulfonato-calixarenes led to a concentration-dependent decrease in the percent time the channel spent in the open state ($P_o$). For example, the concentration of p-tetrasulfonato-calix[4]arene causing a half maximal decrease ($K_1$) in $P_o$ was less than 1 μM.

The very long-duration block periods caused by the n=6 and n=8 compounds made an exact quantitative assessment of the $K_1$ values technically difficult. Therefore, the n=4 derivatives were subsequently used to establish the structure-activity relationship.

Calix[4]arene was found to be completely ineffective at blocking the chloride channel even at a concentration as high as 100 μM. The potency of p-tetrasulfonato-calix[4]arene was tested in the presence of calix[4]arene, and was found to be equal to that that the acid groups are important substituents for channel blockade.

Methylation of p-tetrasulfonato-calix[4]arene to yield 5,11,17,23-tetrasulfonato-25,26,27,28-tetramethoxy-calix [4]arene (TS-TM-calix[4]arene) led to a dramatic improvement in potency. TS-TM-calix[4]arene caused long-lived block periods lasting several hundred seconds at a concentration as low as 3 nM. The long-lived block periods were interrupted by only brief periods of open channel activity suggesting the $K_1$ of the TS-TM-calix[4]arene is subnanomolar. TS-TM-calix[4]arene thus appears to be the most potent chloride channel blocker thus far tested.

The results for some calixarene derivatives tested on chloride channels incorporated into planar lipid bilayers are summarized in Table 1 below. The derivatives in the R, R' and n positions were tested and the maximum block periods as well as the concentrations causing a half-maximal inhibition ($K_i$) were determined.

TABLE 1

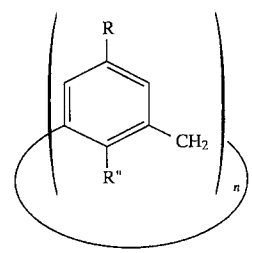

| COMPOUND | n | R | R" | MAXIMUM BLOCK PERIODS (sec) | $K_i$ |
|---|---|---|---|---|---|
| 5,11,17,23-TETRASULFONATO-CALIX[4]ARENE | 4 | $-SO_3Na$ | $-OH$ | 3–4 | 800–900 nM |
| CALIX[4]ARENE | 4 | $-H$ | $-OH$ | NO BLOCK UPTO 100 μM | — |
| 25,26,27,28-TETRAMETHOXY-CALIX[4]ARENE | 4 | $-H$ | $-OCH_3$ | NO BLOCK UPTO 100 μM | — |
| 5,11,17,23-TETRASULFONATO-25,26,27,28-TETRAMETHOXY-CALIX[4]ARENE | 4 | $-SO_3Na$ | $-OCH_3$ | >>100 | <3 nM |
| 5,11,17,23,29,35-HEXASULFONATO-CALIX[6]ARENE | 6 | $-SO_3Na$ | $-OH$ | 30–40 | 400–500 nM |
| 5,11,17,23,29,35,41,47-OCTASULFONATO-CALIX[8]ARENE | 8 | $-SO_3Na$ | $-OH$ | >>100 | <50 nM |

The results tabulated above demonstrate the dependence of blockade on the acidic group in the R position, the increase in potency with an increase in n, and the importance of the R" (R"=OR') constituents on the potency.

Being potent chloride channel blockers, compositions of the calixarene derivatives having acid groups may be used in general to treat respiratory, cardiovascular and gastrointestinal disorders. Specific therapeutic applications for compositions of the calixarene derivatives of the invention include the treatment of asthma, hypertension, cancer, diabetes, ischemia, muscle fatigue, edema, diarrhea, cystic fibrosis and myotonia.

In use, the calixarene derivatives may be admixed with conventional excipients and adjuvants to form a pharmaceutical composition. A pharmaceutically effective amount of the calixarene derivatives is administered to a patient. Although the precise amount and frequency of administration will be selected depending on the specific treatment, typical dosages are 0.5–1.0 mg per kg bodyweight.

Although the present invention has been described by reference to specific embodiments, the scope of the invention is not limited thereto but is defined by reference to the appended claims.

We claim:

1. A composition comprising a calixarene derivative of the formula:

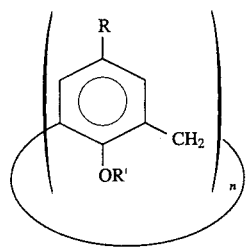

wherein

R is an acidic group selected from the group consisting of $R^1SO_3X$ and $R^1COOX$, wherein X is H, Na, K, Rb, Cs, Li, $NH_4^+$ or $N(R_i)_4^+$ where $R_i$ is H, a $C_{1-4}$ alkyl or an aryl, and $R^1$ is selected from the group consisting of

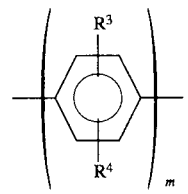

where m=1–2, and $R^3$ and $R^4$ the same or different is each H, a $C_{1-4}$ alkyl or a $C_{1-4}$ alkoxy, and a nitrogen-containing group of the formula

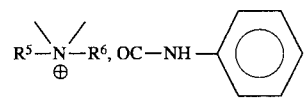

wherein $R^5$ is a $C_{1-4}$ alkyl or a $C_{1-4}$ alkoxy, $R^6$ is a $C_{1-4}$ alkyl or a $C_{1-4}$ alkoxy, and A is

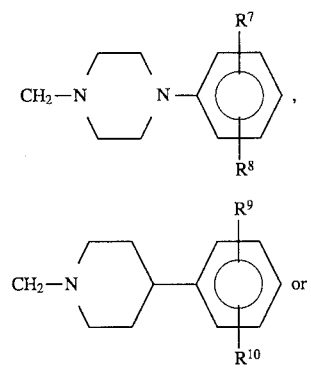

or

17

-continued

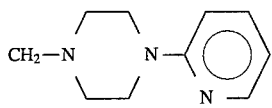

where $R^7$ and $R^8$, the same or different, is each H, a $C_{1-4}$ alkyl or a $C_{1-4}$ alkoxy, and $R^9$ and $R^{10}$, the same or different, is each H, a $C_{1-4}$ alkyl or a $C_{1-4}$ alkoxy;

R' is selected from the group consisting of H, a $C_{1-4}$ alkyl, a $C_{1-4}$ alkoxy, an acid group, an ester group, an aryl, or —$CH_2CONR^5R^6$ where $R^5$ and $R^6$ are as previously defined; and n is an integer of 4–8.

2. A composition according to claim 1, wherein R is $R^1SO_3X$, R' is selected from the group consisting of H and $CH_3$, and n is 4, 6 or 8.

3. A composition according to claim 1, wherein R is $R^1SO_3Na$, $R^1$ is

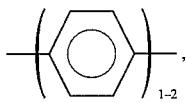

R' is H or $CH_3$, and n is 4, 6 or 8.

18

4. A method of treating respiratory disorders, comprising administering to a patient a therapeutically effective amount of a composition of claim 1, wherein said respiratory disorders are selected from the group consisting of asthma, pulmonary edema and cystic fibrosis.

5. A method as recited in claim 4, wherein said calixarene derivative is a p-sulfonato calixarene.

6. A method of treating cardiovascular disorders, comprising administering to a patient a therapeutically effective amount of a composition of claim 1, wherein said cardiovascular disorders are selected from the group consisting of hypertension, ischemia and cardiovascular edema.

7. A method of treating gastrointestinal disorders, comprising administering to a patient a therapeutically effective amount of a composition of claim 1, wherein said gastrointestinal disorders are selected from the group consisting of diarrhea, irritable bowel syndrome and ulcers.

8. A method of treating skeletal muscle disorders, comprising administering to a patient a therapeutically effective amount of a composition of claim 1, wherein said skeletal muscle disorders are selected from the group consisting of muscle fatigue and myotonia.

\* \* \* \* \*